US011376423B2

(12) United States Patent
Lehmann et al.

(10) Patent No.: US 11,376,423 B2
(45) Date of Patent: Jul. 5, 2022

(54) MEDICAL ELECTROPORATION

(71) Applicants: Torsten Lehmann, Earlwood (AU); Paul Michael Carter, West Pennant Hills (AU); John Michael Heasman, Hampton (AU)

(72) Inventors: Torsten Lehmann, Earlwood (AU); Paul Michael Carter, West Pennant Hills (AU); John Michael Heasman, Hampton (AU)

(73) Assignee: Cochlear Limited, Macquarie University (AU)

( * ) Notice: Subject to any disclaimer, the term of this patent is extended or adjusted under 35 U.S.C. 154(b) by 201 days.

(21) Appl. No.: 16/407,314

(22) Filed: May 9, 2019

(65) Prior Publication Data

US 2019/0351220 A1   Nov. 21, 2019

Related U.S. Application Data

(60) Provisional application No. 62/671,499, filed on May 15, 2018.

(51) Int. Cl.
| A61N 1/05 | (2006.01) |
| A61N 1/32 | (2006.01) |
| A61N 1/36 | (2006.01) |
| A61N 1/378 | (2006.01) |
| A61N 1/04 | (2006.01) |

(52) U.S. Cl.
CPC .......... *A61N 1/0541* (2013.01); *A61N 1/327* (2013.01); *A61N 1/36038* (2017.08); *A61N 1/0412* (2013.01); *A61N 1/3787* (2013.01)

(58) Field of Classification Search
CPC .............................. A61N 1/0541; A61N 1/327
See application file for complete search history.

(56) References Cited

U.S. PATENT DOCUMENTS

| 6,483,806 B1 | 11/2002 | Flickinger et al. |
| 9,533,138 B2 | 1/2017 | Housley |
| 2012/0191032 A1* | 7/2012 | Housley ............. A61K 41/0047 604/20 |
| 2015/0306383 A1* | 10/2015 | Self ...................... A61N 1/3605 607/63 |
| 2016/0012924 A1 | 1/2016 | McClure et al. |
| 2017/0368331 A1 | 12/2017 | Murphy et al. |

FOREIGN PATENT DOCUMENTS

WO    2016205895 A1    12/2016

* cited by examiner

*Primary Examiner* — Michael W Kahelin
*Assistant Examiner* — Naveed R. Kolia
(74) *Attorney, Agent, or Firm* — Edell, Shapiro & Finnan, LLC

(57) ABSTRACT

Presented herein are techniques that enable electroporation of the cells of a recipient of a tissue-stimulating prostheses while the tissue-stimulating prosthesis is implanted in the recipient. Tissue-stimulating prostheses in accordance with embodiments presented herein are configured such that the stimulation electronics (e.g., current sources and integrated circuit) of the prosthesis are not exposed to the high voltages used in electroporation.

24 Claims, 12 Drawing Sheets

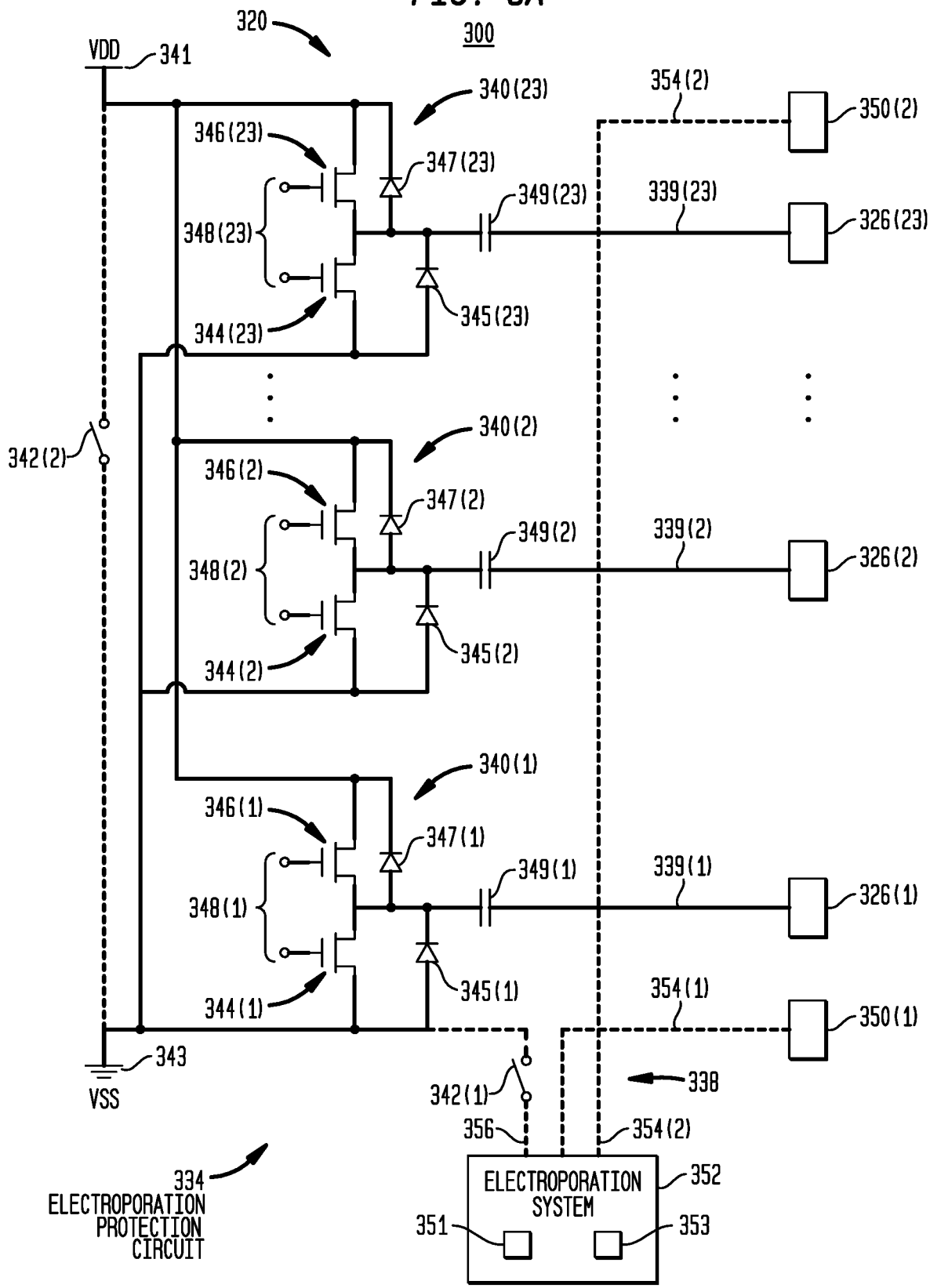

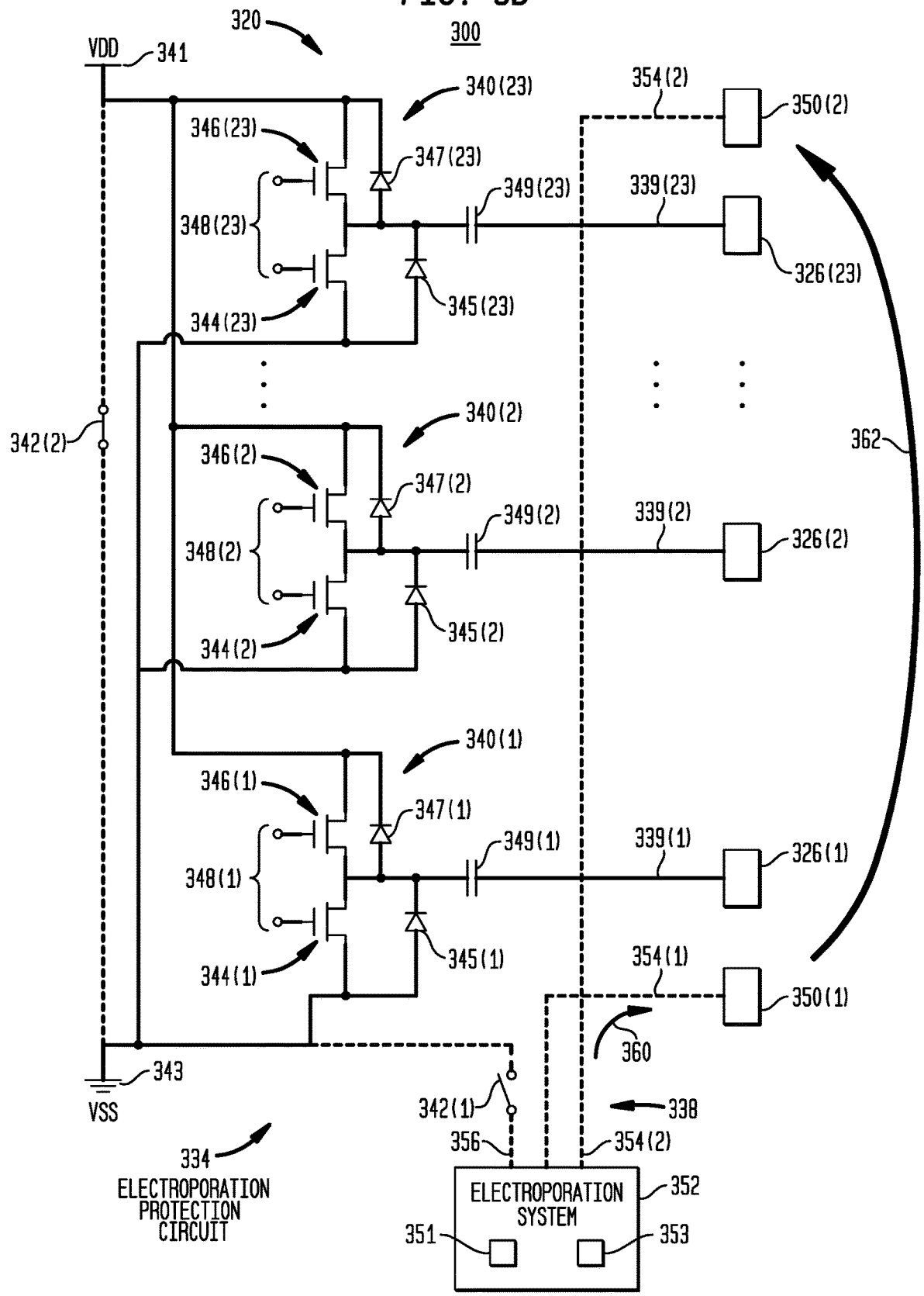

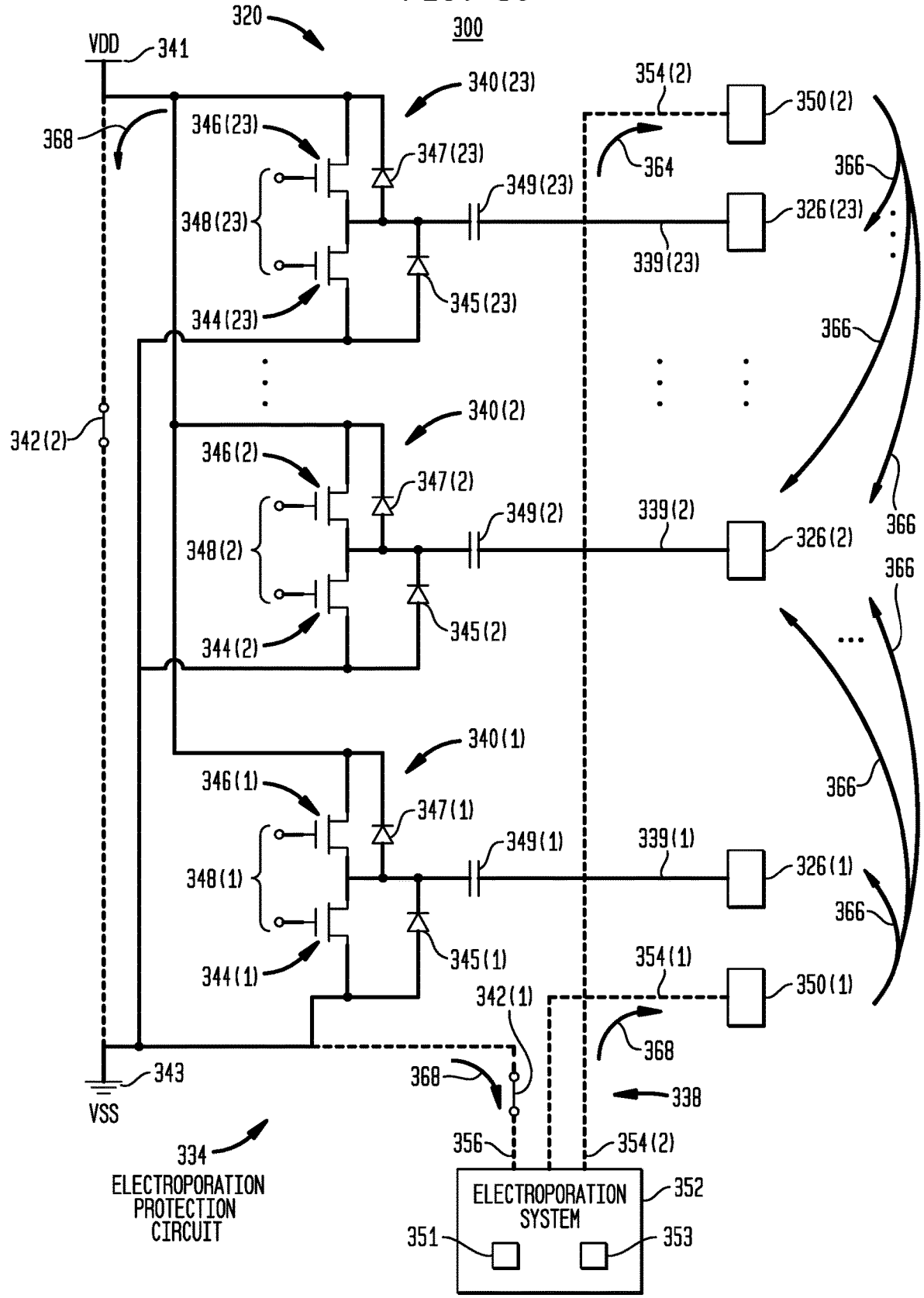

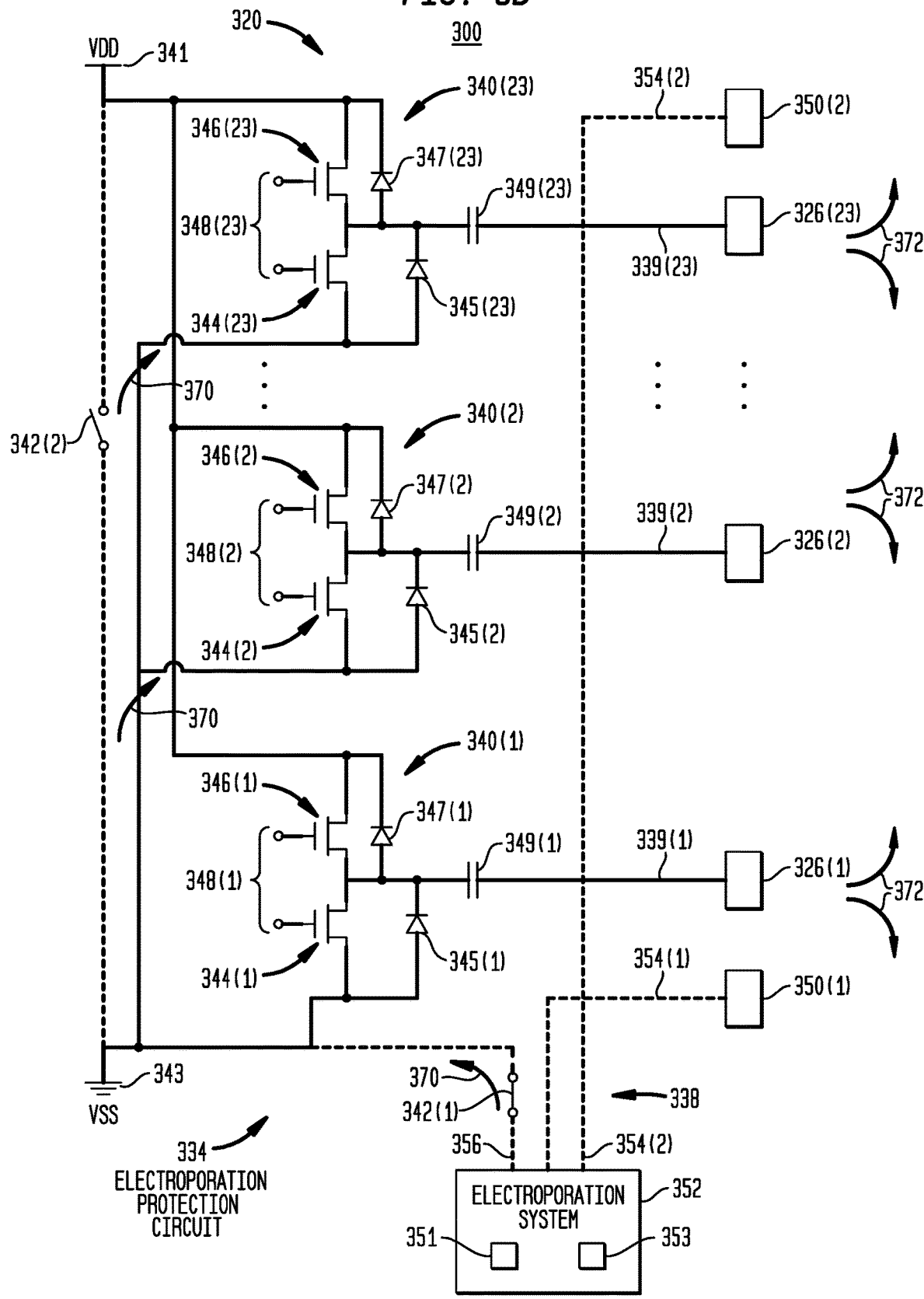

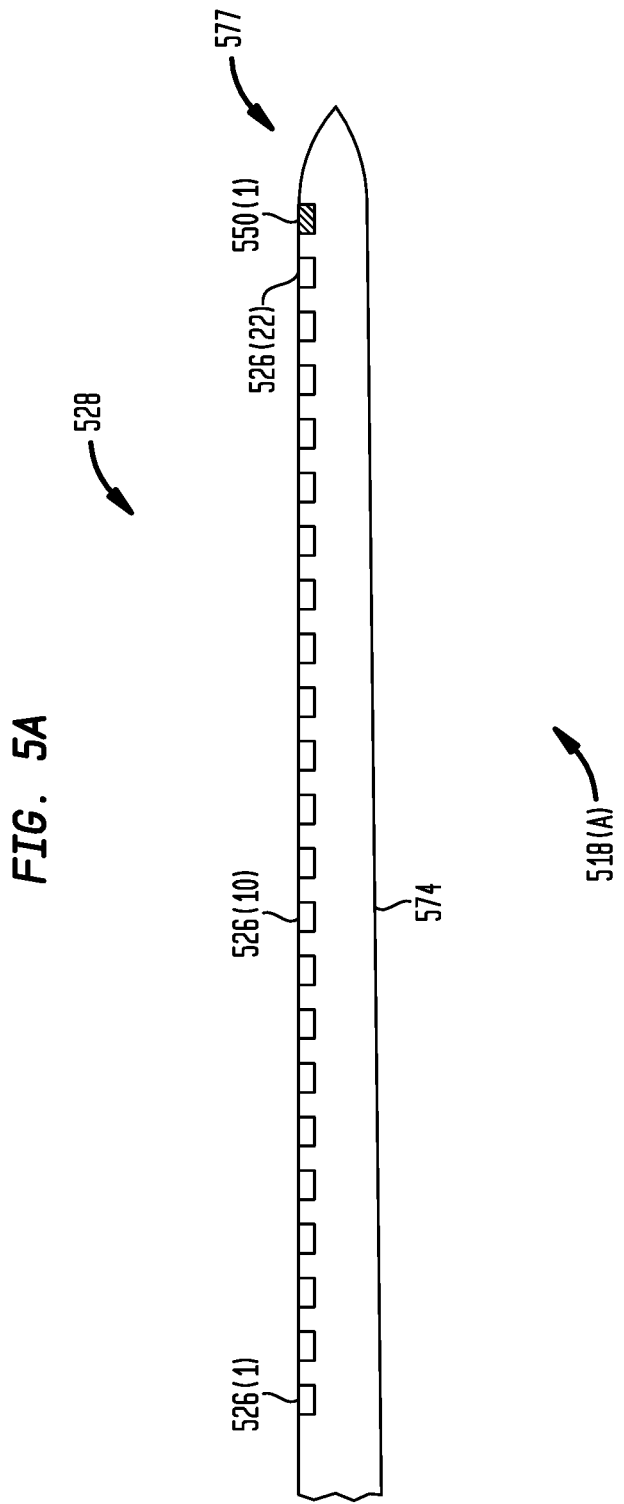

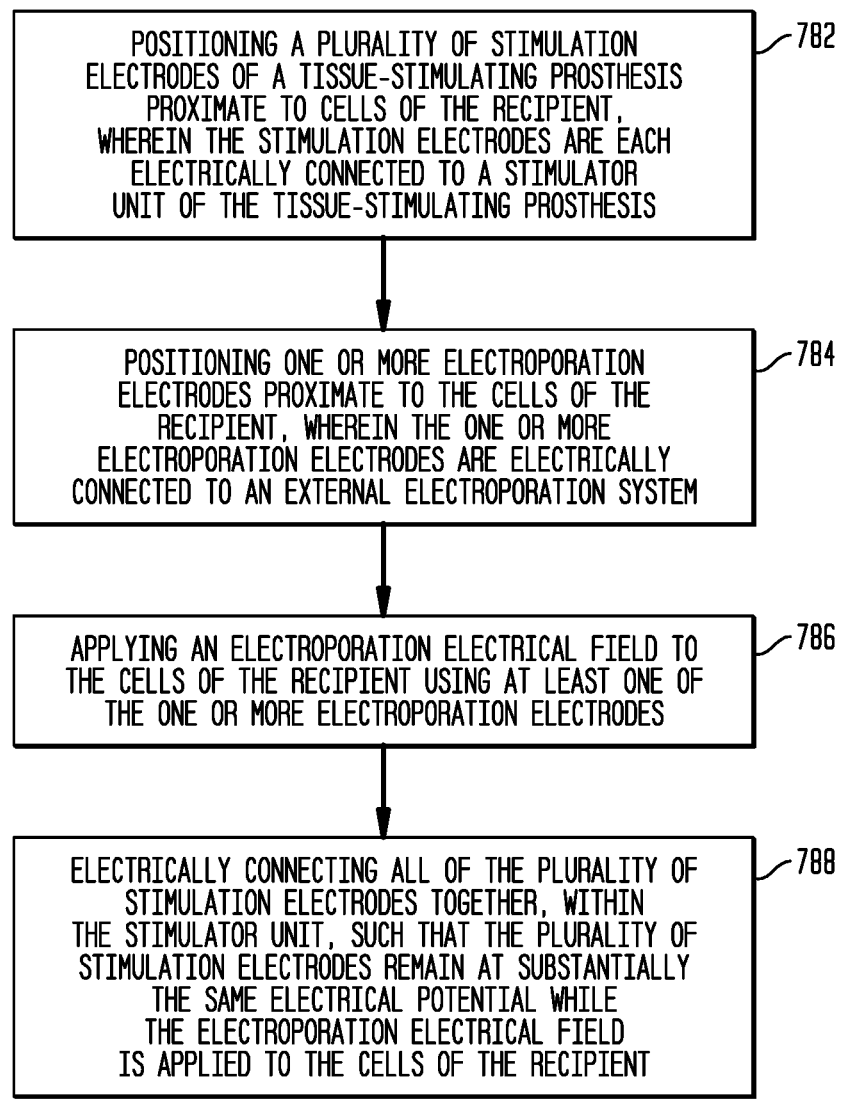

MEDICAL ELECTROPORATION

CROSS-REFERENCE TO RELATED APPLICATION

This application claims the benefit of U.S. Provisional Patent Application No. 62/671,499, filed May 15, 2018, the contents of which is hereby incorporated by reference herein.

BACKGROUND

Field of the Invention

Certain aspects presented herein generally relate to the use of electroporation with tissue-stimulating prostheses.

Related Art

There are several types of medical devices/implants that operate by delivering electrical (current) stimulation to the nerves, muscle, tissue fibers, or other cells of a recipient. These medical devices, sometimes referred to herein as tissue-stimulating prostheses, typically deliver current stimulation to compensate for a deficiency in the recipient. For example, tissue-stimulating hearing prostheses, such as cochlear implants, are often proposed when a recipient experiences sensorineural hearing loss due to the absence or destruction of the cochlear hair cells, which transduce acoustic signals into nerve impulses. Auditory brainstem stimulators are another type of tissue-stimulating hearing prostheses that might be proposed when a recipient experiences sensorineural hearing loss due to damage to the auditory nerve.

SUMMARY

In one aspect, a method is provided. The method comprises: positioning a plurality of stimulation electrodes of a tissue-stimulating prosthesis proximate to cells of the recipient, wherein the stimulation electrodes are each electrically connected to a stimulator unit of the tissue-stimulating prosthesis; positioning one or more electroporation electrodes proximate to the cells of the recipient, wherein the one or more electroporation electrodes are electrically connected to an external electroporation system; applying an electroporation electrical field to the cells of the recipient using at least one of the one or more electroporation electrodes; and electrically connecting all of the plurality of stimulation electrodes together, within the stimulator unit, such that the plurality of stimulation electrodes remain at substantially the same electrical potential while the electroporation electrical field is applied to the cells of the recipient.

In another aspect, a system is provided. The system comprises: at least one electroporation electrode configured to be positioned in a recipient of a tissue-stimulating prosthesis proximate to cells of the recipient; an external electroporation system electrically connected to the at least one electroporation electrode and configured to apply a high-voltage electroporation electrical field to the cells of the recipient using the at least one electroporation electrode; a plurality of stimulation electrodes configured to be positioned in the recipient proximate to the cells of the recipient; and a stimulator unit electrically connected to each of the plurality of stimulation electrodes and comprising stimulation electronics and an electroporation protection circuit configured to ensure that, while the high-voltage electroporation electrical field is applied to the cells of the recipient, the stimulation electronics are only exposed to voltage differences within a predetermined range.

BRIEF DESCRIPTION OF THE DRAWINGS

Embodiments of the present invention are described herein in conjunction with the accompanying drawings, in which:

FIG. 3A is a schematic diagram of a portion of a cochlear implant, in accordance with certain embodiments presented herein;

FIG. 3B is a schematic diagram of a portion of a cochlear implant, in accordance with certain embodiments presented herein;

FIG. 3C is a schematic diagram of a portion of a cochlear implant, in accordance with certain embodiments presented herein;

FIG. 3D is a schematic diagram of a portion of a cochlear implant, in accordance with certain embodiments presented herein;

FIG. 5A is a schematic diagram of a stimulating assembly, in accordance with certain embodiments presented herein;

FIG. 7 is a flowchart of a method, in accordance with certain embodiments presented herein.

DETAILED DESCRIPTION

Figure 1A:
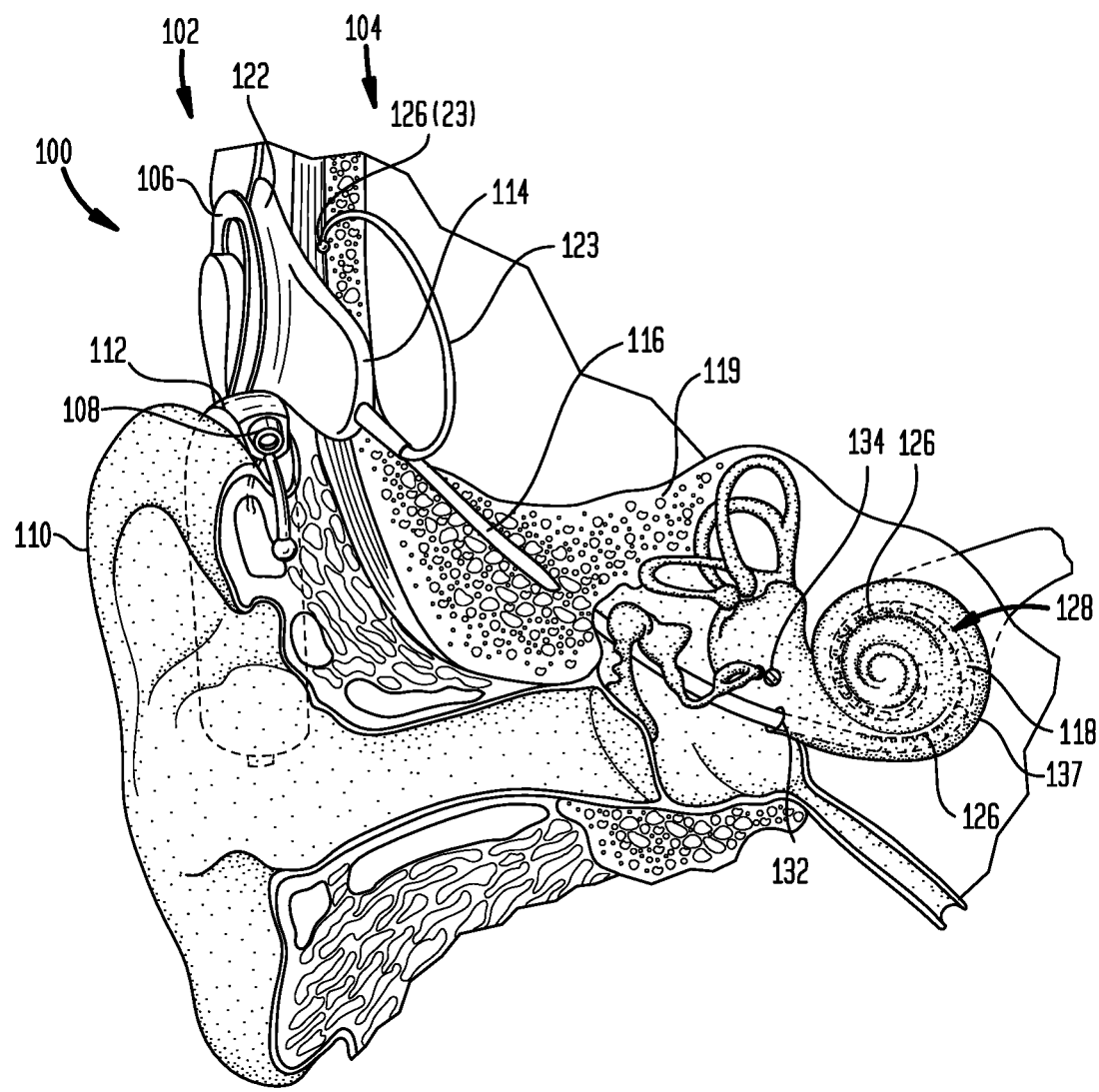
FIG. 1A is a schematic diagram illustrating a cochlear implant, in accordance with certain embodiments presented herein.

Electroporation refers to the application of an electrical field to a cell (e.g., a mesenchymal stem cell) in a manner that creates an electrical potential (i.e., voltage difference) across the cell that, in turn, opens up pores in the membrane of the cell. The electrically opened pores may be used to, for example, allow a treatment substance to enter the cell through the cell membrane (i.e., as the potential difference is applied to the cell, the electrically opened pores in the cell membrane allow material to flow into the cell). After the electrical potential is removed, the pores in the cell membrane close such that the treatment substance remains in the cell. As such, electroporation may be useful with medical implants by altering the biological composition of the cells in a manner that enhances, enables, etc. operation of the medical implants Successful electroporation requires a cell to be exposed to a large electrical field for a sufficient amount of time than enables a desired treatment substance to migrate through the cell membrane. Such an electric field, sometimes referred to herein as an "electroporation electrical field," utilizes a high voltage in the range of, for example, approximately 100 Volts (V) to approximately 150V, over the distance between two or more implanted electrodes positioned in proximity to the target cells (i.e., the cells that are to be electroporated). Such a voltage range is considered "high" because such voltages exceed the typical operating range for electrical components of conventional tissue-stimulating prostheses. That is, conventional tissue stimulating prostheses typically cannot be exposed to such voltages and, as a result, electroporation is generally performed using other devices prior to implantation of a stimulating prostheses into a recipient.

Presented herein are techniques that enable electroporation of the cells of a recipient of a tissue-stimulating prostheses while the tissue-stimulating prosthesis is implanted in the recipient. More specifically, tissue-stimulating prostheses in accordance with embodiments presented herein are configured/arranged such that the stimulation electronics (e.g., current sources and integrated circuit) of the prosthesis are not exposed to the high voltages used in electroporation. In certain embodiments, the tissue-stimulating prostheses presented herein may be used as a delivery and/or return path for generation of the electroporation electrical field As noted, there are several types of tissue-stimulating prostheses that deliver stimulation signals (current signals) to compensate for a deficiency in a recipient. Merely for ease of illustration, the embodiments presented herein are primarily described herein with reference to one type of tissue-stimulating prosthesis, namely a cochlear implant. However, it is to be appreciated that the techniques presented herein may be used with other tissue-stimulating prostheses including, for example, auditory brainstem stimulators, implantable pacemakers, spinal cord stimulators, deep brain stimulators, motor cortex stimulators, sacral nerve stimulators, pudendal nerve stimulators, vagus/vagal nerve stimulators, trigeminal nerve stimulators, retinal or other visual prosthesis/stimulators, occipital cortex implants, diaphragm (phrenic) pacers, pain relief stimulators, other neural or neuromuscular stimulators, etc.

Figure 1B:
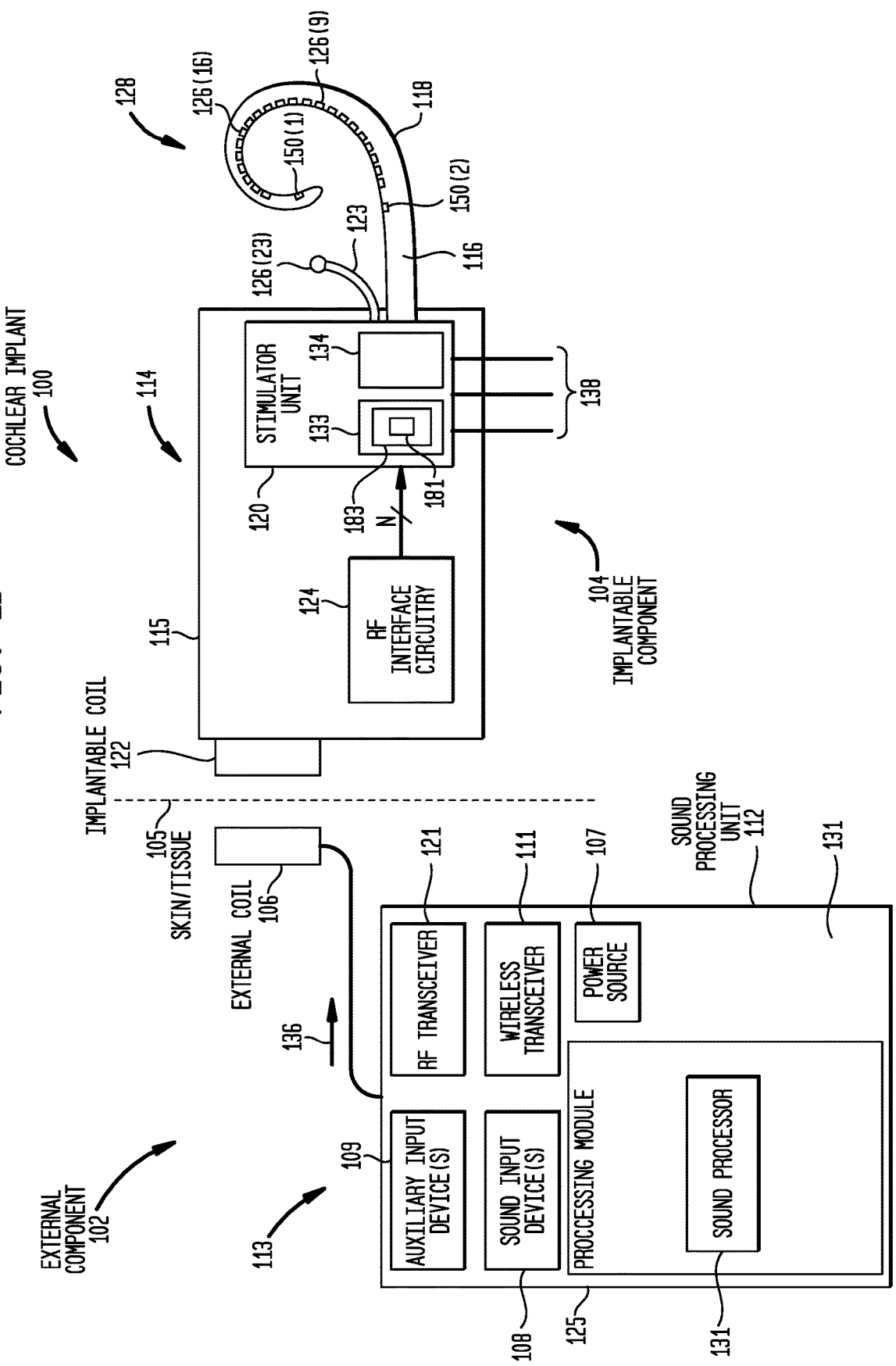
FIG. 1B is a block diagram of the cochlear implant of FIG. 1A.

FIG. 1A is a schematic diagram of an exemplary cochlear implant 100 configured to implement aspects of the techniques presented herein, while FIG. 1B is a block diagram of the cochlear implant 100. For ease of illustration, FIGS. 1A and 1B will be described together.

The cochlear implant 100 comprises an external component 102 and an internal/implantable component 104. The external component 102 is directly or indirectly attached to the body of the recipient and typically comprises an external coil 106 and, generally, a magnet (not shown in FIG. 1) fixed relative to the external coil 106. The external component 102 also comprises one or more input elements/devices 113 for receiving input signals at a sound processing unit 112. In this example, the one or more one or more input devices 113 include sound input devices 108 (e.g., microphones positioned by auricle 110 of the recipient, telecoils, etc.) configured to capture/receive input signals, one or more auxiliary input devices 109 (e.g., audio ports, such as a Direct Audio Input (DAI), data ports, such as a Universal Serial Bus (USB) port, cable port, etc.), and a wireless transmitter/receiver (transceiver) 111, each located in, on, or near the sound processing unit 112.

The sound processing unit 112 also includes, for example, at least one battery 107, a radio-frequency (RF) transceiver 121, and a processing module 125. The processing module 125 may comprise a number of elements, including a sound processor 131.

In the examples of FIGS. 1A and 1B, the sound processing unit 112 is a behind-the-ear (BTE) sound processing unit configured to be attached to, and worn adjacent to, the recipient's ear. However, it is to be appreciated that embodiments of the present invention may be implemented by sound processing units having other arrangements, such as by a button sound processing unit (i.e., a component having a generally cylindrical shape and which is configured to be magnetically coupled to the recipient's head), etc., a mini or micro-BTE unit, an in-the-canal unit that is configured to be located in the recipient's ear canal, a body-worn sound processing unit, etc.

Returning to the example embodiment of FIGS. 1A and 1B, the implantable component 104 comprises an implant body (main module) 114, a lead region 116, and an intra-cochlear stimulating assembly 118, all configured to be implanted under the skin/tissue (tissue) 105 of the recipient. The implant body 114 generally comprises a hermetically-sealed housing 115 in which RF interface circuitry 124 and a stimulator unit 120 are disposed. As described further below, the stimulator unit 120 comprises stimulation electronics 133 and an electroporation protection circuit 134. The stimulation electronics 133 comprises, among other elements, one or more current sources 181 on an integrated circuit (IC) 183.

The implant body 114 also includes an internal/implantable coil 122 that is generally external to the housing 115, but which is connected to the RF interface circuitry 124 via a hermetic feedthrough (not shown in FIG. 1B).

As noted, stimulating assembly 118 is configured to be at least partially implanted in the recipient's cochlea 137. Stimulating assembly 118 includes a plurality of longitudinally spaced intra-cochlear electrical contacts (electrodes) 126 that collectively form a contact or electrode array 128 configured to, for example, deliver electrical stimulation signals (current signals) to the recipient's cochlea and/or to sink stimulation signals from the recipient's cochlea. FIG. 1A illustrates a specific arrangement in which stimulating assembly 118 comprises twenty-two (22) intra-cochlear electrodes 126, labeled as electrodes 126(1) through 126(22). It is to be appreciated that embodiments presented herein may be implemented in alternative arrangements having different numbers of intra-cochlear electrodes.

Stimulating assembly 118 extends through an opening in the recipient's cochlea (e.g., cochleostomy, the round window, etc.) and has a proximal end connected to stimulator unit 120 via lead region 116 and a hermetic feedthrough (not shown in FIG. 1B). Lead region 116 includes a plurality of conductors (wires) that electrically couple the electrodes 126 to the stimulator unit 120.

Also shown in FIG. 1A is an extra-cochlear electrode 126(23). The extra-cochlear electrode 126(23) is an electrical contact that is configured to, for example, deliver electrical stimulation to the recipient's cochlea and/or to sink current from the recipient's cochlea. The extra-cochlear electrode 126(23) is connected to a reference lead 123 that includes one or more conductors that electrically couple the extra-cochlear electrode 126(23) to the stimulator unit 120.

As described further below, the intra-cochlear electrodes 126(1)-126(22) and the extra-cochlear electrode 126(23) may be used post-operatively to stimulate the cochlea 137 of the recipient (i.e., operate as delivery or return paths for current signals to the cochlea 137) that evoke a hearing perception. As such, for ease of description, the intra-cochlear electrodes 126(1)-126(22) and the extra-cochlear electrode 126(23) are sometimes referred to herein as "stimulation electrodes."

FIGS. 1A and 1B also illustrate that the stimulating assembly 118 includes two (2) electroporation electrodes 150(1) and 150(2). As described further below, the electroporation electrodes 150(1) and 150(2) are electrically connected to an external electroporation system (not shown in FIGS. 1A and 1B) and are used exclusively to electroporate the recipient's cochlea nerve cells during implantation of the stimulating assembly 118 into the cochlea 137. That is, the electroporation electrodes 150(1) and 150(2) may be configured to source, sink, or both source and sink electroporation signals that result in the application of an electroporation electrical field to the nerve cells of the cochlea 137. Thereafter, the electroporation electrodes 150(1) and 150(2) can be electrically isolated from the electroporation system (e.g., electrically disconnected).

Electroporation may have a number of associated purposes. In certain examples, the electroporation is used to open the pores in the cells in the presence of treatment substances to enable the treatment substances to enter the cells. As used herein, "treatment substances" may include, but are not limited to, biological or bioactive substances, chemicals, pharmaceutical agents, nanoparticles, ions, Deoxyribonucleic acid (DNA) DNA cassettes or plasmid, Ribonucleic acid (RNA) molecules, proteins such as Brain-derived neurotrophic factors, peptides, RNAi, etc. Therefore, in accordance with certain embodiments, prior to electroporation, a treatment substance may first be delivered to the cochlea 137. Such a treatment substance may be delivered in a number of different manners, such as through an implantation tool, substance delivery device (e.g., lumen, syringe, etc.), a coating on the stimulating assembly 118, etc.

As noted, the cochlear implant 100 includes the external coil 106 and the implantable coil 122. The coils 106 and 122 are typically wire antenna coils each comprised of multiple turns of electrically insulated single-strand or multi-strand platinum or gold wire. Generally, a magnet is fixed relative to each of the external coil 106 and the implantable coil 122. The magnets fixed relative to the external coil 106 and the implantable coil 122 facilitate the operational alignment of the external coil with the implantable coil. This operational alignment of the coils 106 and 122 enables the external component 102 to transmit data, as well as possibly power, to the implantable component 104 via a closely-coupled wireless link formed between the external coil 106 with the implantable coil 122. In certain examples, the closely-coupled wireless link is a radio frequency (RF) link. However, various other types of energy transfer, such as infrared (IR), electromagnetic, capacitive and inductive transfer, may be used to transfer the power and/or data from an external component to an implantable component and, as such, FIG. 1B illustrates only one example arrangement.

As noted above, sound processing unit 112 includes the processing module 125. The processing module 125 is configured to convert input audio signals into stimulation control signals 136 for use in stimulating a first ear of a recipient (i.e., the processing module 125 is configured to perform sound processing on input audio signals received at the sound processing unit 112). Stated differently, the sound processor 131 (e.g., one or more processing elements implementing firmware, software, etc.) is configured to convert the captured input audio signals into stimulation control signals 136 that represent stimulation signals for delivery to the recipient. The input audio signals that are processed and converted into stimulation control signals may be audio signals received via the sound input devices 108, signals received via the auxiliary input devices 109, and/or signals received via the wireless transceiver 111.

In the embodiment of FIG. 1B, the stimulation control signals 136 are provided to the RF transceiver 121, which transcutaneously transfers the stimulation control signals 136 (e.g., in an encoded manner) to the implantable component 104 via external coil 106 and implantable coil 122. That is, the stimulation control signals 136 are received at the RF interface circuitry 124 via implantable coil 122 and provided to the stimulator unit 120. The stimulator unit 120 is configured to utilize the stimulation control signals 136 to generate stimulation signals (e.g., current signals) for delivery to the recipient's cochlea via one or more stimulation electrodes 126(1)-126(22). In this way, cochlear implant 100 electrically stimulates the recipient's auditory nerve cells, bypassing absent or defective hair cells that normally transduce acoustic vibrations into neural activity, in a manner that causes the recipient to perceive one or more components of the input audio signals.

One of the performance-limiting factors in modern cochlear implants is the distance between the intra-cochlear electrodes and the corresponding stimulated spiral ganglion cells. Due to the confining bony structure of the cochlea, insertion of a stimulation electrode array is comparatively easy, safe and provides a stable body-implant interface, all of which have contributed to the success of the cochlear implant. In addition, advanced mechanical designs has given small improvements in performance. However, one of the key performance-limiting factors in modern cochlear implants is the distance between the stimulating intra-cochlear electrodes and the corresponding stimulated spiral ganglion cells. If the distance between electrodes and the stimulated spiral ganglion cells could be reduced, it may be possible to, for example: have more stimulation sites delivering better frequency discrimination to the recipient, use lower stimulation current and, accordingly, reduce implant power consumption, and/or use lower stimulation voltage, and, accordingly reduce implant size and power dissipation. It has been proposed to inject neural growth factors into the cochlea during surgery to entice the nerves to grow towards the stimulation electrodes. However, the injected neural growth factors generally dissipate before any significant benefit is obtained. One possible solution to this key problem is to insert neural growth factor genes into cells in the cochlear via cell electroporation during surgical implantation of an intra-cochlear stimulating assembly.

As noted, electroporation refers to the application of an electrical field to a cell such that pores are opened in the cell membrane. When these cells are opened in the presence of a treatment substances, such as neural growth factor genes, the treatment substances may enter the cell through the cell membrane. After the electrical potential is removed, the pores in the cell membrane close such that the treatment substances remains in the cell.

Also as noted, successful electroporation requires a cell to be exposed to a large electrical field utilizing a voltage that is sufficiently high, such as a voltage in the range of approximately 100 Volts (V) to approximately 150V, which may damage conventional cochlear implants, namely the stimulation electronics. For this reason, conventional techniques generally rely on the use of a dedicated electroporation array that is temporarily inserted into the cochlea during surgery and used for only the electroporation procedure. The dedicated electroporation array is then removed from the cochlea, after which a normal intra-cochlear stimulating array is inserted. Insertion of electrode arrays into the delicate cochlea is always a risk to the recipient, and it is therefore desirable to have only one insertion procedure during surgery. As such, presented herein are techniques that enable electroporation of the cochlea nerve cells while the cochlear implant is implanted in the recipient by isolating the stimulation electronics from the high voltages used during the electroporation.

More specifically, referring to the arrangement of FIGS. 1A and 1B, as noted the stimulator unit 120 comprises stimulation electronics 133 and an electroporation protection circuit 134. The stimulator unit 120 may be electrically connected to the external electroporation system via one or more connections 138. Similarly, the electroporation electrodes 150(1) and 150(2) are also electrically connected to the external electroporation system (e.g., via connections 138 or separate connections). The electroporation electrodes 150(1) and 150(2) are used to electroporate the recipient's cochlea nerve cells during implantation of the stimulating assembly 118 into the cochlea 137 (i.e., used during application of an electroporation electrical field to the cochlea). While the electroporation electrical field is applied to the cochlea 137, the electroporation protection circuit 134 operates to ensure that the stimulation electronics 133 are not exposed to the high electroporation voltages. In certain embodiments, the electroporation protection circuit 134 operates, during electroporation, to hold all of the stimulation electrodes (i.e., intra-cochlear electrodes 126(1)-126(22) and extra-cochlear electrode 126(23)) at approximately the same potential (e.g., within approximately the range of the voltage across two diodes, as within a range of approximately 1.4V).

Figure 2:
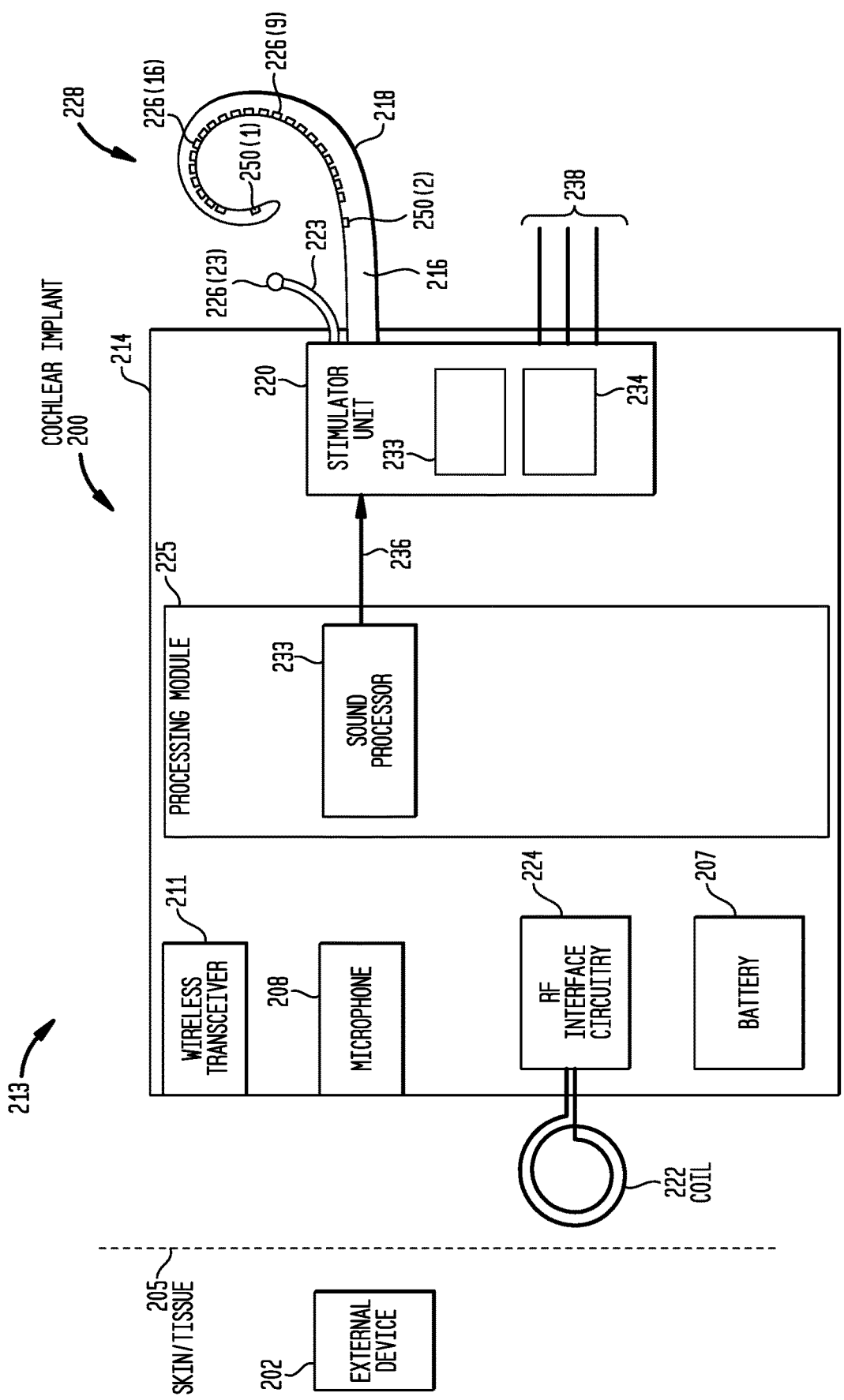
FIG. 2 is a block diagram of a totally implantable cochlear implant, in accordance with certain embodiments presented herein.

FIGS. 1A and 1B illustrate an arrangement in which the cochlear implant 100 includes an external component. However, it is to be appreciated that embodiments of the present invention may be implemented in cochlear implants having alternative arrangements. For example, FIG. 2 is a functional block diagram of an exemplary totally implantable cochlear implant 200 configured to implement embodiments of the present invention. Since the cochlear implant 200 is totally implantable, all components of cochlear implant 200 are configured to be implanted under skin/tissue 205 of a recipient. Because all components are implantable, cochlear implant 200 operates, for at least a finite period of time, without the need of an external device. An external device 202 can be used to, for example, charge an internal power source (battery) 207. External device 202 may be a dedicated charger or a conventional cochlear implant sound processor.

Cochlear implant 200 includes an implant body (main implantable component) 214, one or more input elements 213 for capturing/receiving input audio signals (e.g., one or more implantable microphones 208 and a wireless transceiver 211), an implantable coil 222, and an elongate intra-cochlear stimulating assembly 218.

The stimulating assembly 218 is substantially similar to stimulating assembly 218 described above with reference to FIGS. 1A and 1B. That is, stimulating assembly 218 is configured to be at least partially implanted in the recipient's cochlea and includes a plurality of longitudinally spaced electrodes 226(1)-226(22) that collectively form a contact or electrode array 228, as well as electroporation electrodes 250(1) and 250(2). Lead region 216 includes a plurality of conductors (wires) that electrically couple the electrodes 226 and 250 to the stimulator unit 220.

Similarly, cochlear implant 200 also comprises an extra-cochlear electrode 226(23), which is substantially similar to extra-cochlear electrode 126(23) described above with reference to FIGS. 1A and 1B. That is, extra-cochlear electrode 226(23) is connected to a lead 223 that includes one or more conductors that electrically couple the extra-cochlear electrode 226(23) to the stimulator unit 220.

The microphone 208 and/or the implantable coil 222 may be positioned in, or electrically connected to, the implant body 214. The implant body 214 further comprises the battery 207, RF interface circuitry 224, a processing module 225, and a stimulator unit 220 (which is similar to stimulator unit 120 of FIGS. 1A and 1B). The processing module 225 may be similar to processing module 125 of FIGS. 1A and 1B, and includes sound processor 231.

In the embodiment of FIG. 2, the one or more implantable microphones 208 are configured to receive input audio signals. The processing module 225 is configured to convert received signals into stimulation control signals 236 for use in stimulating a first ear of a recipient. Stated differently, sound processor 231 is configured to convert the input audio signals into stimulation control signals 236 that represent electrical stimulation for delivery to the recipient.

As noted above, FIGS. 1A and 1B illustrate an embodiment in which the external component 102 includes the processing module 125. As such, in the illustrative arrangement of FIGS. 1A and 1B, the stimulation control signals 136 are provided to the implanted stimulator unit 120 via the RF link between the external coil 106 and the internal coil 122. However, in the embodiment of FIG. 2 the processing module 225 is implanted in the recipient. As such, in the embodiment of FIG. 2, the stimulation control signals 236 do not traverse the RF link, but instead are provided directly to the stimulator unit 220. The stimulator unit 220 is configured to utilize the stimulation control signals 236 to generate electrical stimulation signals that are delivered to the recipient's cochlea via one or more stimulation channels.

In addition, the stimulator unit 220 comprises stimulation electronics 233 and an electroporation protection circuit 234. The stimulator unit 220 may be electrically connected to an external electroporation system (not shown in FIG. 2) via one or more connections 238. Similarly, the electroporation electrodes 250(1) and 250(2) are also electrically connected to the external electroporation system (e.g., via connections 238 or separate connections). The electroporation electrodes 250(1) and 250(2) are used to electroporate the recipient's cochlea nerve cells during implantation of the stimulating assembly 218 into the cochlea (i.e., used during application of an electroporation electrical field to the cochlea). While the electroporation electrical field is applied to the cochlea, the electroporation protection circuit 234 operates to ensure that the stimulation electronics 233 are not exposed to the high electroporation voltages. In certain embodiments, the electroporation protection circuit 234 operates, during electroporation, to hold all of the stimulation electrodes (i.e., intra-cochlear electrodes 226(1)-226(22) and extra-cochlear electrode 226(23)) at approximately the same potential (e.g., within approximately the range of the voltage across two diodes, as within a range of approximately 1.4V).

As noted, the techniques presented herein may be implemented in a number of different types of tissue-stimulating prostheses. However, merely for ease of description, further details of the techniques presented herein will generally be described with reference to cochlear implants.

FIG. 3A is a simplified schematic diagram of a portion of a cochlear implant 300, in accordance with embodiments presented herein. Similar to the embodiments of FIGS. 1A, 1B, and 2, cochlear implant 300 comprises a stimulator unit 320 and a stimulating assembly 318.

In the embodiment of FIG. 3A, the stimulating assembly 318 comprises twenty-two (22) electrodes 326, referred to individually as intra-cochlear electrodes 326(1)-326(22). Although not shown in FIG. 3A, the electrodes 326(1)-326(22) may be disposed in an electrically-insulating body (carrier member) configured for insertion into a cochlea of a recipient. The electrodes 326(1)-326(22) are connected to the stimulator unit 320 via conductors 339(1)-339(22), respectively, which extend through a lead region (not shown in FIG. 3A). For ease of illustration, only two electrodes and the respective conductors, namely electrodes 326(1)/326(2) and conductors 339(1)/339(2), are shown in FIG. 3A.

FIG. 3A also illustrates that the cochlear implant 300 includes at least one extra-cochlear electrode. For ease of description, a single extra-cochlear electrode, referred to as electrode 326(23), is shown in FIG. 3A. Collectively, the intra-cochlear electrodes 326(1)-326(22) and the extra-cochlear electrode 326(23) are referred to as "stimulation electrodes" 326(1)-326(23).

Also similar to the embodiments of FIGS. 1A, 1B, and 2, the stimulator unit 320 comprises stimulation electronics (not shown in FIG. 3A) and an electroporation protection circuit 334. The stimulator unit 320 also comprises a stimulation power supply (VDD) rail/node 341 and a stimulation ground (VSS) rail/node 343. During implantation of the cochlear implant 300, the stimulator unit 320 is deactivated and, as such, no power is supplied at the stimulation power supply node 341 during implantation and, accordingly, during electroporation (which occurs toward the end of the implantation procedure).

The electroporation protection circuit 334 is comprised of several elements shown in FIG. 3A. In particular, the electroporation protection circuit 334 includes a plurality of stimulation switches 340, referred to individually as stimulation switches 340(1)-340(23) and one or more electroporation switches 342, referred to individual as electroporation switches 342(1) and 342(2). For ease of illustration, only stimulation switches 340(1), 340(2), and 340(23) are shown in FIG. 3A.

Each of the stimulation switches 340(1)-340(23) is associated with, and electrically connected to, one of the electrodes 326(1)-326(23), respectively (i.e., via respective conductors 339(1)-339(23)). The stimulation switches 340(1)-340(23) each include a first transistor 344 and second transistor 346. The first transistor 344 comprises a first diode 345, while the second transistor 346 comprises a second diode 347. That is, stimulation switch 340(1) includes a first transistor 344(1) with a first diode 345(1), stimulation switch 340(2) includes a first transistor 344(2) with a first diode 345(2), and so on. Similarly, stimulation switch 340(1) includes a second transistor 346(1) with a second diode 347(1), stimulation switch 340(2) includes a second transistor 346(2) with a second diode 347(2), and so on. The stimulation switches 340(1)-340(23) also each include respective connections, referred to as connections 348(1)-348(23), to the stimulation electronics (e.g., integrated circuit, current sources, etc.) of the stimulator unit 320. For ease of illustration, the stimulation electronics have been omitted from FIG. 3A. In certain embodiments, electrode coupling capacitors 349(1)-349(23) may be positioned between each of the stimulation switches 340(1)-340(23) and the respective electrode 326(1)-326(23).

As noted, the electroporation protection circuit 334 also comprises electroporation switches 342(1) and 342(2), which are selectively used during the electroporation process. As described further below, the specific configuration/state (i.e., open or closed) of each of the electroporation switches 342(1) and 342(2) during electroporation may vary depending on, for example, the direction of current applied to generate an electroporation electrical field.

Also shown in FIG. 3A are two (2) electroporation electrodes 350(1) and 350(2) and an external (i.e., non-implanted) electroporation system 352. In this example, the electroporation electrodes 350(1) and 350(2) are directly electrically connected to the electroporation system 352 via respective conductors 354(1) and 354(2). The electroporation system 352 comprises, among other components, one or more high-voltage current sources 351 and a ground node 353.

In certain embodiments, the electroporation electrodes 350(1) and 350(2) may be integrated into the same electrically-insulating body as the intra-cochlear electrodes 326(1)-326(22). In these embodiments, the conductors 354(1) and 354(2) may extend through the stimulator unit 320 for connection to the electroporation system 352. However, in such embodiments, the conductors 354(1) and 354(2), and thus the electroporation electrodes 350(1) and 350(2), do not have any electrical connections to the stimulation electronics (i.e., the electroporation electrodes 350(1) and 350(2) are electrically isolated from the stimulation electronics).

It is to be appreciated that integration of the electroporation electrodes 350(1) and 350(2) into the same electrically-insulating body as the intra-cochlear electrodes 326(1)-326(22) is one illustrative arrangement. In other embodiments, the electroporation electrodes 350(1) and 350(2) may be physically separate from the carrier member in which the intra-cochlear electrodes 326(1)-326(22) are disposed. In such embodiments, the conductors 354(1) and 354(2) may not extend through the stimulator unit 320 for connection to the electroporation system 352.

In the example of FIG. 3A, there are several connections 338 between the external electroporation system 352 and the implanted components. In particular, as noted, two of the connections 338 are formed by conductors 354(1) and 354(2), which connect the electroporation electrodes 350(1) and 350(2), respectively, to the electroporation system 352. In addition, a third connection is formed by conductor 356 that connects the electroporation system 352 to electroporation switch 342(1) in the stimulator unit 320.

One of the primary purposes of the electroporation protection circuit 334 is to enable the stimulator unit 320 to conduct some of the high-voltage electroporation signals, while also ensuring that, during electroporation, the stimulation electronics are not exposed to the high electroporation voltages (since expose to these voltages would damage the stimulation electronics). The high-voltage electroporation signals, which are used to generate the electroporation electrical field, may be at least partially sourced via the stimulator unit 320, at least partially sunk via the stimulator unit 320, or neither sourced nor sunk via the stimulator unit 320. These and other variations are described further below with reference to FIGS. 3B, 3C, and 3D.

Referring specifically to FIG. 3B, shown is a first arrangement in which the electroporation protection circuit 334 is configured to electrically connect all of the plurality of stimulation electrodes 326(1)-326(23) together, within the stimulator unit 320, such that the plurality of stimulation electrodes remain at substantially the same electrical potential while the electroporation electrical field is applied (e.g., by shorting all of the electrodes 326(1)-326(23) to the stimulation ground node 343 or some other suitable implant potential so that the electrodes all remain within the same voltage range of one another). In the example of FIG. 3B (as well as those of FIGS. 3C and 3D, described below), the electroporation protection circuit 334 maintains each of the stimulation electrodes 326(1)-326(23) within an electrical potential range that is approximately less than or equal to the range of the voltage across two diodes, such as within a range of approximately 1.4V.

In FIG. 3B, as shown by arrows 360, the high-voltage electroporation signals are delivered to the cochlea (not shown in FIG. 3B) via electroporation electrode 350(1). As shown by arrows 362, the electroporation electrode 350(2) functions as a return path for the high-voltage electroporation signals to a ground node of the electroporation system 352. In addition, electroporation switch 342(1) is closed to short the stimulation power supply node 341 to the stimulation ground node 343. As such, the protection diodes 345(1)-345(23) and 347(1)-347(23) ensure that the stimulation electronics are only exposed to minimal voltage potential differences (which constitutes an effective short).

Referring next to FIG. 3C, shown is one arrangement in which the electrodes 326(1)-326(23) could be used as one terminal in the electroporation process. For example, as shown by arrows 364, the high-voltage electroporation signals are delivered to the cochlea (not shown in FIG. 3C) via electroporation electrodes 350(1) and 350(2). As shown by arrows 366, the electrodes 326(1)-326(23) function as a return path for the electroporation high-voltage electroporation signals to a ground node of the electroporation system 352, where the electroporation signals pass through the stimulator unit 320.

In FIG. 3C, the electroporation signals received at the electrodes 326(1)-326(23) enter the stimulation switches 340(1)-340(23) at nodes 363(1)-363(23) and subsequently exit the stimulation switches via diodes 347(1)-347(23), respectively. The diodes 347(1)-347(23) are connected to the stimulation power supply node 341, which is turn connected to the stimulation ground node 343 via closed switch 342(2). In addition, switch 342(1) is also closed so as to connect the stimulation ground node 343 to conductor 356, which in turn is connected to the ground node of the electroporation system 352. Therefore, as shown by arrows 368, the electroporation signals pass from diodes 347(1)-347(23) to the stimulation power supply node 341, the stimulation ground node 343, and then to the ground node of the electroporation system 352 via switch 342(1). In this example, the protection diodes 345(1)-345(23) and 347(1)-347(23) ensure that the stimulation electronics cannot be exposed to voltage potential differences of more than a few volts.

In embodiments that include electrode coupling capacitors 349(1)-349(23), shorting the electrodes 326(1)-326(23) during electroporation will enable these capacitors to share the electroporation current (when the electrodes 326(1)-326(23) are used as one terminal for the electroporation). This will reduce the voltage build-up on the capacitors 349(1)-349(23), and hence make it unnecessary for these capacitors to be high-voltage tolerant components.

FIG. 3C illustrates an arrangement of the electroporation protection circuit 334 when the electrodes 326(1)-326(23) function as a return path for the electroporation signals. However, the electroporation protection circuit 334 may be configured to provide bi-directional protection of the stimulation electronics such that the electrodes 326(1)-326(23) may also be used to deliver the electroporation signals to the cochlea. Such an arrangement is shown in FIG. 3D.

More specifically, in the embodiment of FIG. 3D, switch 342(1) is closed and the conductor 356 is connected to a high voltage current source of the electroporation system 352, rather than to a ground node. In addition, the conductors 354(1) and 354(2) are each connected to a ground node of the electroporation system 352. Therefore, as shown by arrows 370, during electroporation current flows from conductor 356 through switch 342(1), then through diodes 345(1)-345(23) and into the recipient's tissue. As shown by arrows 372, the electroporation electrodes 350(1) and 350(2) then function as a return path to the ground of the electroporation system (i.e., via conductors 354(1) and 354(2)).

FIGS. 3A-3D have been described with reference to an electroporation protection circuit 334 that includes two electroporation switches, namely switches 341(1) and 342(2). It is to be appreciated that, in certain embodiments, switch 341(2) may be eliminated and switch 341(1) may be made selectively connectable to either the stimulation power supply node 341 or the stimulation ground node 343.

For example, if conductor 356 is used as the electroporation source and one or more of the electroporation electrodes 350(1) or 350(2) are used to as a return path, then no current is conducted through switch 342(2) and it becomes redundant. If the opposite polarity of electroporation signals is utilized (e.g., electroporation electrodes 350(1) or 350(2) are at a higher potential than the electrodes 326(1)-326(23)), then switch 342(1) could equally be configured to connect to the stimulation power supply node 341 rather than the stimulation ground node 343. If the electrodes 326(1)-326(23) are left floating while electroporation is performed between electroporation electrodes 350(1) and 350(2), then current will need to flow through between the stimulation power supply node 341 and the stimulation ground node 343 to ensure that the electrodes remain within a given potential range of one another. However, the stimulation power supply node 341 and the stimulation ground node 343 could be connected together with small capacitor in parallel with a Zener diode. Therefore, if switch 342(2) were not present, the capacitor would allow current to flow between the stimulation power supply node 341 and the stimulation ground node 343, perhaps not exceeding a few volts during an electroporation pulse. In addition, if the capacitor does not charge up to over the voltage of the Zener diode, then the Zener diode would start conducting in the same manner as a switch.

In summary, FIGS. 3A-3D illustrate arrangements in which the electroporation protection circuit 334 enables the electroporation system 352 to apply a large electroporation voltage at the cochlea, without exposing the implant electronics to high voltage differences (e.g., the stimulation electronics are only exposed to voltage differences within a predetermined range, such as that of approximately two diode voltage drops). That is, the electroporation protection circuit 334 is configured to electrically connect all of the plurality of stimulation electrodes 326(1)-326(23) together, within the stimulator unit 320, such that the plurality of stimulation electrodes 326(1)-326(23) remain at substantially the same electrical potential while the electroporation electrical field is applied.

The electroporation voltage may be applied between the implant electrodes 326(1)-326(23) and either or both of the electroporation electrodes 350(1) and 350(2), between the electroporation electrodes 350(1) and 350(2) themselves, etc.

FIGS. 3A-3D illustrate arrangements in which the stimulator unit 320 includes at least one connection, and possibly up to three connections, to the external electroporation system 352. After electroporation, these electrical connections to the external electroporation system 352 will be severed and their exposed ends covered by an insulating material (e.g., a silicone cap) as a precaution only (i.e., the exposed ends will have no electrical connections to the implant and will likely present a high impedance).

Figure 4:
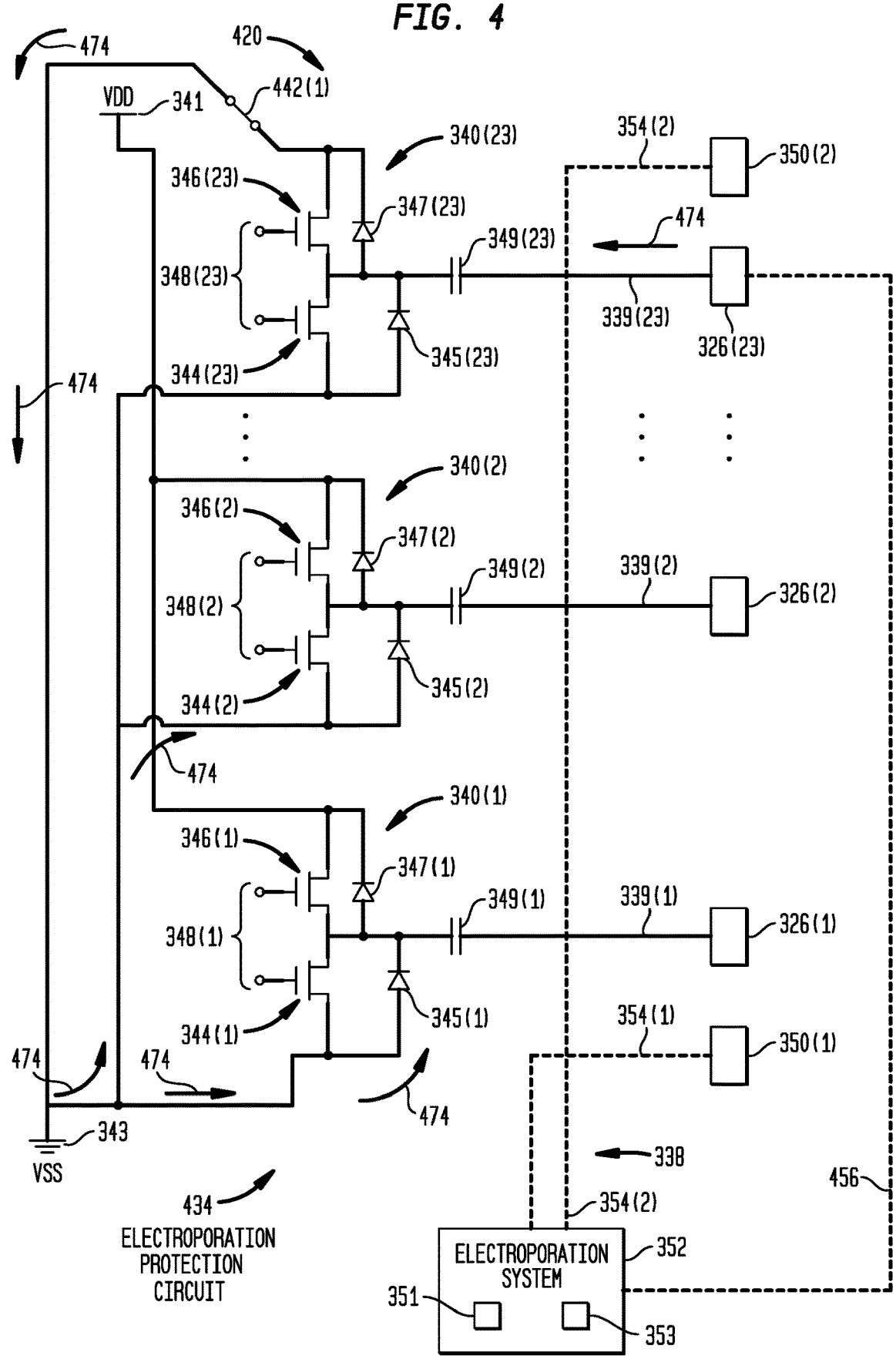
FIG. 4 is a schematic diagram of a portion of a cochlear implant, in accordance with certain embodiments presented herein.

As noted, FIGS. 3A-3D illustrate arrangements in which the stimulator unit 320 includes at least one connection to the external electroporation system 352 via conductor 356. It is to be appreciated that, in other arrangements, external electroporation system 352 could instead be connected to the implant via the extra-cochlear electrode 326(23), thereby eliminating conductor 356 and an associated extra can feed-through. FIG. 4 illustrates one such arrangement.

More specifically, FIG. 4 illustrates a stimulator unit 420 that includes an electroporation protection circuit 434. The electroporation protection circuit 434 is comprised of several elements shown in FIG. 4. In particular, the electroporation protection circuit 434 comprises stimulation switches 340(1)-340(23), as described above with reference to FIG. 3A, and an electroporation switch 442(1). Similar to the above embodiments, the stimulation switches 340(1)-340(23) are connected to electrodes 326(1)-326(23), respectively. For ease of illustration, only stimulation switches 340(1), 340(2), and 340(23), as well as corresponding electrodes 326(1), 326(2), and 326(23), are shown in FIG. 4. Also present in the arrangement of FIG. 4 are the electroporation electrodes 350(1) and 350(2).

In the embodiment of FIG. 4, a current source of the electroporation system 352 is electrically connected to the extra-cochlear electrode 326(23) via at least a conductor 456. During electroporation (i.e., when electroporation signals are delivered from the electroporation system 352 to the extra-cochlear electrode 326(23)), node 473, which is located between diodes 345(23) and 347(23), will take a high voltage corresponding to the voltage of the electroporation signals (e.g., 100 V-150V). As shown by arrows 474, the electroporation signals will then be conducted through diode 347(23) to node 471.

In FIG. 4, the electroporation switch 442(1) can be activated to as connect output node 471 to either the stimulation power supply node 341 or the stimulation ground node 343, depending on the polarity of the electroporation signals. In the illustrative example of FIG. 4, electroporation switch 442(1) is closed so as to connect the node 471 to the stimulation ground node 343. As such, as shown by arrows 474, the electroporation signals will pass to, and then through, the diodes 345(1)-345(22) of the other stimulation switches 340(1)-340(22) to the corresponding electrodes 326(1)-326(22). The electroporation signals can then be recovered via the electroporation electrodes 350(1)-350(2), which are connected to a ground node of the electroporation system 352 via conductors 354(1) and 354(2), respectively.

FIG. 4 has been described with reference to one example current flow direction. It is to be appreciated that current could also flow in the opposite direction. In such an arrangement, the electroporation switch 442(1) would be closed so as to connect the node 471 to the stimulation power supply node 341.

As noted above, certain embodiments presented herein may use of electrodes that are dedicated for use during electroporation only (i.e., electroporation electrodes), as well as intra-cochlear electrodes and one or more extra-cochlear electrodes (collectively stimulation electrodes that may be used post-operatively for stimulating the cochlea of a recipient). Also as noted above, the electroporation electrodes may be integrated into the same carrier member (e.g., silicone or elastomer body) as the intra-cochlear electrodes. Incorporating electroporation electrodes into the same carrier member as the intra-cochlear electrodes may make the geometry (and hence the electrical field which governs the electroporation process) well-defined during electroporation. However, in other embodiments the electroporation electrodes may be physically separate from the carrier member in which the intra-cochlear electrodes are disposed (e.g., part of an insertion tool, separate electrodes, etc.).

Figure 5B:
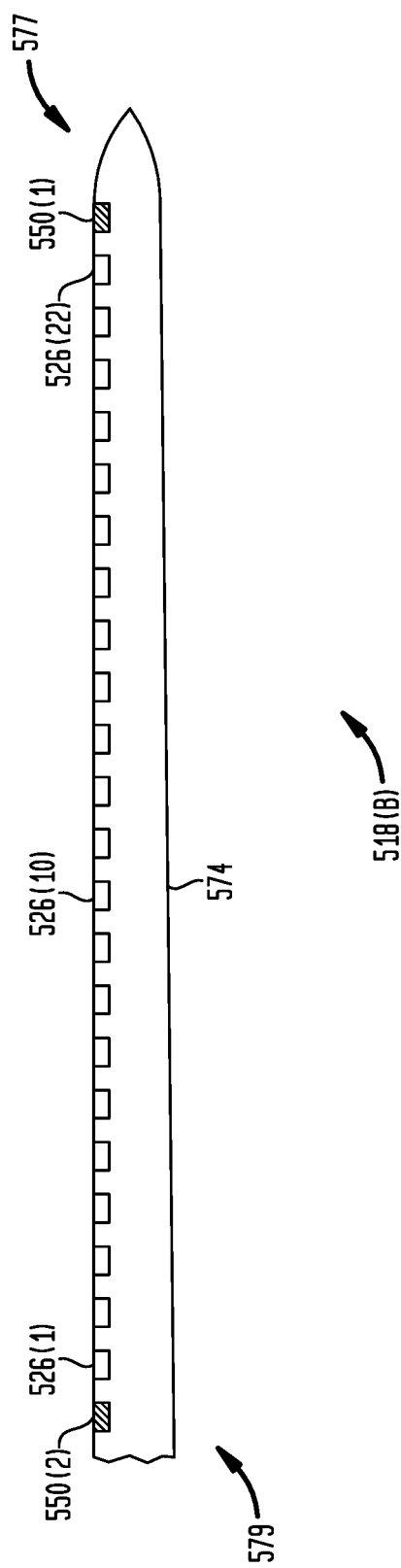
FIG. 5B is a schematic diagram of a stimulating assembly, in accordance with certain embodiments presented herein.

FIGS. 5A and 5B illustrate example arrangements in which electroporation electrodes are integrated with intra-cochlear electrodes. Referring first to FIG. 5A, shown is a simplified schematic view of a stimulating assembly 518(A) configured to be implanted in the cochlea of a recipient. FIG. 5A illustrates a specific arrangement in which stimulating assembly 518(A) comprises twenty-two (22) intra-cochlear electrodes 526, labeled as electrodes 526(1) through 526(22). The intra-cochlear electrodes 526(1)-526(22) form an electrode array 528. It is to be appreciated that embodiments presented herein may be implemented in alternative arrangements having different numbers of intra-cochlear electrodes.

As shown, intra-cochlear electrode 526(1) is the most basal/proximal intra-cochlear electrode, while intra-cochlear electrode 526(22) is the most distal/apical intra-cochlear electrode. The intra-cochlear electrodes 526(1)-526(22) are each disposed in an electrically-insulating carrier member or body 576 formed, for example, from an elastomer or other resiliently flexible material. The electrodes 526(1)-526(22) are all connected to a stimulator unit via conductors that extend through the body 576 of the stimulating assembly 518(A) and a lead region. For ease of illustration, the conductors, lead region, and stimulator unit have all been omitted from FIG. 5A.

FIG. 5A also illustrates that an electroporation electrode 550(1) is positioned at a distal end (tip) 577 of the body 576. The electroporation electrode 550(1) is connected to an external electroporation system (not shown) via the stimulator unit. However, unlike the electrodes 526(1)-526(22), the electroporation electrode 550(1) is isolated from any stimulation electronics (e.g., at least one conductor extends from the electroporation electrode 550(1), through the body 576, and through the stimulator unit to the electroporation system). In such embodiments, after electroporation, the electroporation electrode 550(1) can be electrically isolated from the electroporation system (e.g., electrically disconnected by severing the connection thereto).

In one example, the arrangement of FIG. 5A may be used in a progressive electroporation process. That is, electroporation signals could be delivered repeatedly, periodically, etc., via electroporation electrode 550(1) as the stimulating assembly 518(A) is inserted into the cochlea. As a result, electroporation could take place along the entire length of the cochlea (at different points in time during the insertion). Progressive electroporation may also be used with other arrangements.

Referring next to FIG. 5B, shown is a simplified schematic view of a stimulating assembly 518(B) configured to be implanted in the cochlea of a recipient. The stimulating assembly 518(B) is similar to that shown in FIG. 5A in that the stimulating assembly 518(B) comprises twenty-two (22) intra-cochlear electrodes 526, labeled as electrodes 526(1) through 526(22), and electroporation electrode 550(1) positioned at the distal end 577 of the body 576. However, in this specific example, the stimulating assembly 518(B) also comprises a second electroporation electrode 550(2) positioned at a proximal end 579 of the body 576. The electroporation electrode positions shown in FIG. 5B may be used, for example, to provide electroporation at two locations (e.g., distal and proximal) in the cochlea.

The electroporation electrodes 550(1) and 550(2) are connected to an external electroporation system (not shown) via the stimulator unit. However, unlike the electrodes 526(1)-526(22), the electroporation electrodes 550(1) and 550(2) are isolated from any stimulation electronics (e.g., one or more conductors extend from the electroporation electrodes 550(1)/550(2), through the body 576, and through the stimulator unit to the electroporation system). In such embodiments, after electroporation, the electroporation electrodes 550(1) and 550(2) can be electrically isolated from the electroporation system (e.g., electrically disconnected by severing the connection thereto).

It is to be appreciated that electroporation electrode positions shown in FIGS. 5A and 5B are illustrative and that electroporation electrodes could be incorporated into a stimulating assembly at other locations. For example, two electroporation electrodes could be placed at the distal end of the stimulating assembly body. In such embodiments, electroporation signals could be provided between these two electrodes before a sufficient amount of the intra-cochlear stimulation electrodes are inserted. At deeper insertion, the two electroporation electrodes on the tip could be ganged for more flexible control of the electrical field. Alternatively, one or more electroporation electrodes could also or alternatively be incorporated at or near a mid-point of the stimulating assembly.

Figure 6:
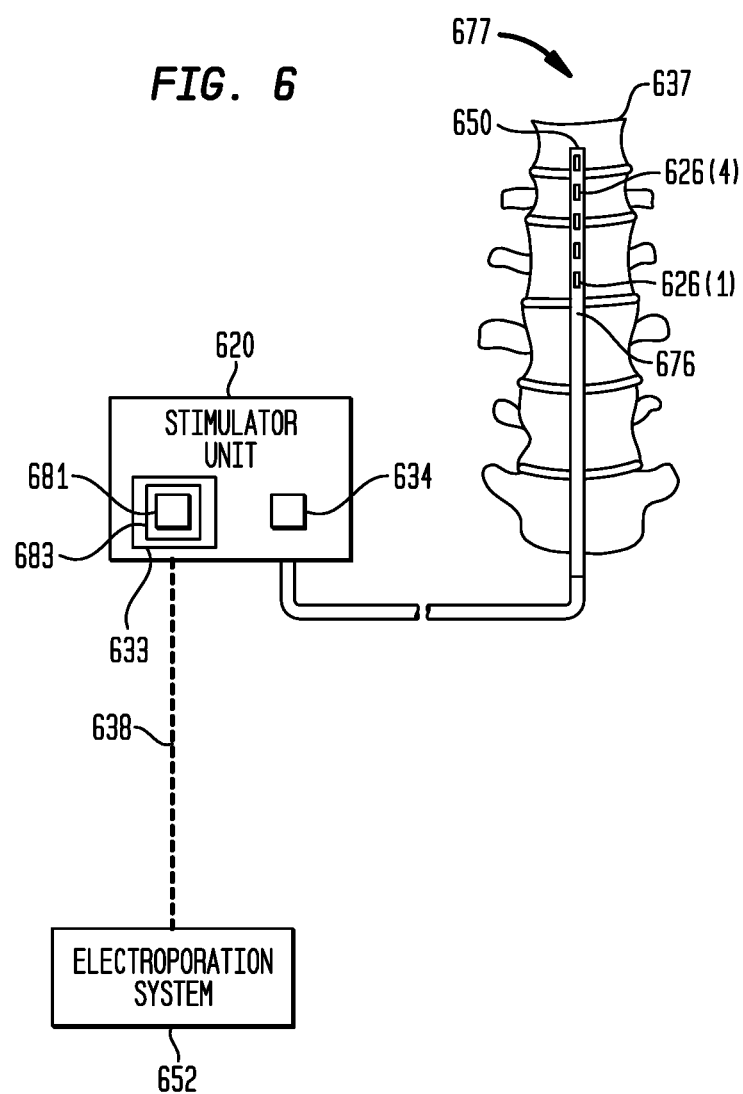
FIG. 6 is a schematic diagram of a spinal cord stimulator, in accordance with certain embodiments presented herein.

Embodiments presented herein have primarily been described with reference to cochlear implants. However, as noted elsewhere wherein, the techniques presented herein may also or alternatively be used with other types of tissue stimulating prostheses (e.g., auditory brainstem stimulators, implantable pacemakers, spinal cord stimulators, deep brain stimulators, motor cortex stimulators, sacral nerve stimulators, pudendal nerve stimulators, vagus/vagal nerve stimulators, trigeminal nerve stimulators, retinal or other visual prosthesis/stimulators, occipital cortex implants, diaphragm (phrenic) pacers, pain relief stimulators, other neural or neuromuscular stimulators, etc.). FIG. 6 is a simplified schematic diagram illustrating an example spinal cord stimulator 600 in which embodiments presented herein may be implemented.

The spinal cord stimulator 600 comprises a stimulator unit 620 and a stimulating assembly 618. The stimulating assembly 618 is implanted in a recipient adjacent/proximate to the recipient's spinal cord 627 and comprises four (4) stimulation electrodes 626, referred to as stimulation electrodes 626(1)-626(4). The stimulation electrodes 626(1)-626(4) are disposed in an electrically-insulating body 676 and are electrically connected to the stimulator 620 via conductors (not shown) that extend through the electrically-insulating body 676. The stimulating assembly 618 also comprises an electroporation electrode 650, which is disposed at the distal end 677 of the body 676. Similar to the stimulation electrodes 626(1)-626(4), the electroporation electrode 650 is also electrically connected to the stimulator 620 via at least one conductor (not shown) that extends through the body 676.

The stimulator unit 620 may be configured similar to stimulator units 120, 220, 320, etc. described above. As such, stimulator unit 620 comprises stimulation electronics 633 and an electroporation protection circuit 634. The stimulation electronics 633 may comprise, among other elements, one or more current sources 681 on an integrated circuit (IC) 683.

Following implantation, the stimulation electronics 633, generate stimulation signals for delivery to the spinal cord 627 via stimulation electrodes 626(1)-626(4). Although not shown in FIG. 6, an external controller may also be provided to transmit signals through the recipient's skin/tissue to the stimulation electronics 633 for control of the stimulation signals.

Similar to the embodiments described above, the stimulator unit 620 is electrically connected to an external electroporation system 652. During implantation of the stimulating assembly 618, the external electroporation system 652 may use the electroporation electrode 650 to apply an electroporation electrical field to nerve cells in or near the spinal cord 637. Use of the electroporation electrode 650 to apply an electroporation electrical field may include, for example, using the electroporation electrode 650 as a delivery path or return path for high-voltage electroporation signals. While the electroporation electrical field is applied, the electroporation protection circuit 634 is configured to hold/maintain the stimulation electrodes 626(1)-626(4) at approximately the same electrical potential (e.g., by shorting all of the electrodes 626(1)-626(4) to a stimulation ground node or some other suitable implant potential so that the electrodes all remain within the same voltage range of one another). In the example of FIG. 6, the electroporation protection circuit 634 maintains each of the stimulation electrodes 626(1)-626(4) within an electrical potential range that is approximately less than or equal to the range of the voltage across two diodes, such as within a range of approximately 1.4V.

FIG. 7 is a flowchart of a method 780 in accordance with certain embodiments presented herein. Method 780 begins at 782 where a plurality of stimulation electrodes of a tissue-stimulating prosthesis are positioned proximate to cells of the recipient. The stimulation electrodes are each electrically connected to a stimulator unit of the tissue-stimulating prosthesis. At 784, one or more electroporation electrodes are positioned proximate to the cells of the recipient, where the one or more electroporation electrodes are electrically connected to an external electroporation system. At 786, an electroporation electrical field is applied to the cells of the recipient using at least one of the one or more electroporation electrodes. At 788, all of the plurality of stimulation electrodes are electrically connected together within the stimulator unit such that the plurality of stimulation electrodes remain at substantially the same electrical potential while the electroporation electrical field is applied to the cells of the recipient.

It is to be appreciated that the above described embodiments are not mutually exclusive and that the various embodiments can be combined in various manners and arrangements.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A method, comprising:
   positioning a plurality of stimulation electrodes of a tissue-stimulating prosthesis proximate to cells of a recipient, wherein the stimulation electrodes are each electrically connected to one or more current sources included in a stimulator unit of the tissue-stimulating prosthesis;
   positioning one or more electroporation electrodes proximate to the cells of the recipient, wherein the one or more electroporation electrodes are electrically connected to an external electroporation system via the stimulator unit, wherein the stimulator unit comprises an electroporation protection circuit comprising a plurality of switches;
   applying high-voltage electroporation signals to the cells of the recipient using at least one of the one or more electroporation electrodes, where the high-voltage electroporation signals are at least one of sourced to the at least one of the one or more electroporation electrodes or sunk from the at least one of the one or more electroporation electrodes via the stimulator unit; and selectively actuating one or more switches in the electroporation protection circuit to isolate the one or more current sources while the high-voltage electroporation signals pass through the stimulator unit.

2. The method of claim 1, further comprising:
after applying the high-voltage electroporation signals, using one or more of the plurality of stimulation electrodes to deliver stimulation signals to the cells of the recipient.

3. The method of claim 1, wherein selectively actuating one or more switches in the electroporation circuit to isolate the one or more current sources while the high-voltage electroporation signals pass through the stimulator unit comprises:
electrically connecting all of the plurality of stimulation electrodes together, within the stimulator unit, such that while the high-voltage electroporation signals are applied to the cells of the recipient, the current sources are only exposed to voltage differences within a predetermined range approximately 1.4V.

4. The method of claim 1, wherein applying the high-voltage electroporation signals using at least one of the one or more electroporation electrodes comprises:
generating high-voltage electroporation signals at the external electroporation system; and delivering the high-voltage electroporation signals to the cells of the recipient via the stimulator unit and at least one of the one or more electroporation electrodes.

5. The method of claim 4, wherein the one or more electroporation electrodes comprise two or more electroporation electrodes, and wherein the method further comprises:
delivering the high-voltage electroporation signals to the cells of the recipient via the stimulator unit and at least a first one of the two or more electroporation electrodes; and
returning the high-voltage electroporation signals from the cells of the recipient to the external electroporation system via the stimulator unit and at least a second one of the two or more electroporation electrodes, wherein the at least second one of the two or more electroporation electrodes is different from the at least first one of the two or more electroporation electrodes.

6. The method of claim 4, further comprising:
returning the high-voltage electroporation signals from the cells of the recipient to the external electroporation system via the plurality of stimulation electrodes and the stimulator unit.

7. The method of claim 1, wherein applying the high-voltage electroporation signals using at least one of the one or more electroporation electrodes comprises:
generating the high-voltage electroporation signals at the external electroporation system;
delivering the high-voltage electroporation signals to the cells of the recipient via the stimulator unit and at least one of the plurality of stimulation electrodes; and
returning the high-voltage electroporation signals from the cells of the recipient to the external electroporation system via at least one of the one or more electroporation electrodes.

8. The method of claim 1, wherein the stimulation electrodes and the one or more electroporation electrodes are all integrated into a single insulating-body, and wherein positioning the plurality of stimulation electrodes proximate to cells of the recipient and positioning the one or more electroporation electrodes proximate to the cells of the recipient, comprises:
inserting the single insulating-body into the recipient at a location proximate to the cells of the recipient.

9. The method of claim 8, further comprising:
after applying the high-voltage electroporation signals, electrically isolating the one or more electroporation electrodes.

10. The method of claim 8, wherein at least one of the one or more electroporation electrodes is disposed at a distal end of the insulating-body.

11. The method of claim 1, further comprising:
after applying the high-voltage electroporation signals, repositioning the one or more electroporation electrodes; and
applying one or more further electroporation signals using at least one of the one or more repositioned electroporation electrodes.

12. The method of claim 1, wherein selectively actuating one or more switches in the electroporation circuit to isolate the one or more current sources while the high-voltage electroporation signals pass through the stimulator unit comprises:
electrically connecting all of the plurality of stimulation electrodes together such that the plurality of stimulation electrodes remain within a predetermined potential range while the high-voltage electroporation-signals are applied to the cells of the recipient.

13. A system, comprising:
at least one electroporation electrode configured to be positioned in a recipient of a tissue-stimulating prosthesis proximate to cells of the recipient;
a plurality of stimulation electrodes configured to be positioned in the recipient proximate to the cells of the recipient;
a stimulator unit electrically connected to each of the plurality of stimulation electrodes and the electroporation electrodes, wherein the stimulator unit comprises an electroporation protection circuit and stimulation electronics including one or more current sources; and
an external electroporation system electrically connected to the at least one electroporation electrode via the stimulator unit and configured to apply high-voltage electroporation signals to the cells of the recipient, wherein the high-voltage electroporation signals are at least one of sourced to the at least one electroporation electrode or sunk from the at least one electroporation electrode via the stimulator unit;
wherein the electroporation protection circuit is configured to enable the high-voltage electroporation signals to pass through the stimulator unit while isolating the one or more current sources from the high-voltage electroporation signals.

14. The system of claim 13, wherein the electroporation protection circuit is configured to maintain the plurality of stimulation electrodes within a potential range of approximately 1.4 V while the high-voltage electroporation signals are applied to the cells of the recipient.

15. The system of claim 14, wherein the electroporation protection circuit is configured to connect each of the plurality of stimulation electrodes to a ground node of the stimulator unit while the high-voltage electroporation signals are applied to the cells of the recipient.

16. The system of claim 13, wherein the electroporation protection circuit, comprises:

a plurality of stimulation switches connecting the current sources to the plurality of stimulation electrodes and each connected between a stimulation power supply node and a stimulation ground node of the stimulator unit; and one or more electroporation switches configured to selectively connect one or both of the stimulation power supply node and the stimulation ground node to the external electroporation system.

17. The system of claim 13, wherein to apply the high-voltage electroporation signals using the at least one electroporation electrode, the external electroporation system is configured to generate and deliver the high-voltage electroporation signals to the cells of the recipient via the stimulator unit and the at least one electroporation electrode.

18. The system of claim 17, wherein the at least one electroporation electrode comprises two or more electroporation electrodes, and wherein to apply the high-voltage electroporation signals using the at least one electroporation electrode, the external electroporation system is configured to generate and deliver the high-voltage electroporation signals to the cells of the recipient via at least a first one of the two or more electroporation electrodes, wherein the at least a second one of the two or more electroporation electrodes is configured to function as a return path for the high-voltage electroporation signals from the cells of the recipient to the external electroporation system, and wherein the at least second one of the two or more electroporation electrodes is different from the at least first one of the two or more electroporation electrodes.

19. The system of claim 17, wherein the plurality of stimulation electrodes and the stimulator unit are configured to function as a return path for the high-voltage electroporation signals from the cells of the recipient to the external electroporation system.

20. The system of claim 17, wherein to apply the high-voltage electroporation signals using the at least one electroporation electrode, the external electroporation system is configured to generate and the deliver high-voltage electroporation signals to the cells of the recipient via the stimulator unit and at least one of the plurality of stimulation electrodes.

21. The system of claim 13, wherein the stimulation electrodes and the at least one electroporation electrode are all integrated into a single insulating-body.

22. The system of claim 21, wherein the at least one electroporation electrode is disposed at a distal end of the insulating-body.

23. The system of claim 21, wherein the at least one electroporation electrode comprises a plurality of electroporation electrodes.

24. The system of claim 13, wherein a first electrode of the at least one electroporation electrode is a source of the high-voltage electroporation signals and a second electrode of the at least one electroporation electrode is a sink of the high voltage electroporation electrical field, and wherein an electroporation switch shorts, based on the one or more signals received via the electrical connection to the external electroporation system, a stimulation power supply node to a stimulation ground node such that the stimulation electrodes remain at within a predetermined potential range while the high-voltage electroporation-signals are applied to the cells of the recipient.

* * * * *